United States Patent [19]
Duff

[11] Patent Number: 4,611,582
[45] Date of Patent: Sep. 16, 1986

[54] VERTEBRAL CLAMP
[75] Inventor: Thomas A. Duff, Madison, Wis.
[73] Assignee: Wisconsin Alumni Research Foundation, Madison, Wis.
[21] Appl. No.: 565,283
[22] Filed: Dec. 27, 1983
[51] Int. Cl.[4] ............................. A61F 5/00; A61F 5/04
[52] U.S. Cl. .................................... 128/69; 128/92 R; 128/92 EA
[58] Field of Search ............. 128/69, 92 A, 346, 92 R, 128/92 EA

[56] References Cited

U.S. PATENT DOCUMENTS

| | | | |
|---|---|---|---|
| 2,474,401 | 6/1981 | Miskew | 128/69 |
| 4,041,939 | 8/1977 | Hall | 128/69 |
| 4,361,141 | 11/1982 | Tanner | 128/69 |
| 4,369,769 | 1/1983 | Edwards | 128/69 |
| 4,386,603 | 6/1983 | Mayfield | 128/69 |
| 4,401,112 | 8/1983 | Rezaian | 128/92 E |
| 4,448,191 | 5/1984 | Rodnyansky et al. | 128/92 R |

Primary Examiner—Gene Mancene
Assistant Examiner—C. W. Shedd
Attorney, Agent, or Firm—David J. Houser

[57] ABSTRACT

A vertebral clamp adapted to control the spatial relationship between two vertebrae by attachment to the laminae thereof. The vertebral clamp includes a longitudinally extending body divided into first and second halves. The halves are fastened together by fastening means that allow for adjustment of the length of the body. Two laminar clamps are attached to the body, one at each end thereof. Each laminar clamp is adapted to rigidly and securely clamp from opposed sides to a lamina of one of the vertebrae with the other laminar clamp similarly clamped to a lamina of the other vertebra.

12 Claims, 5 Drawing Figures

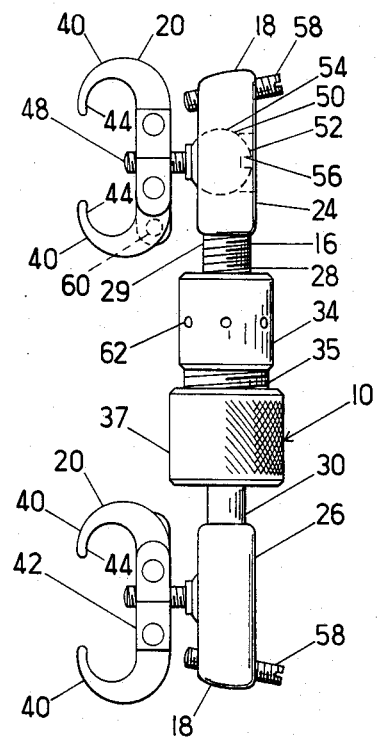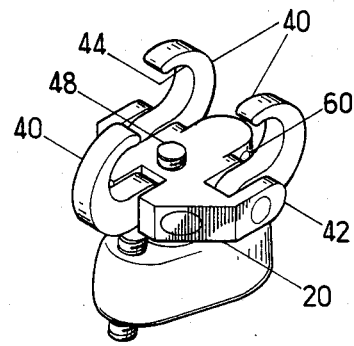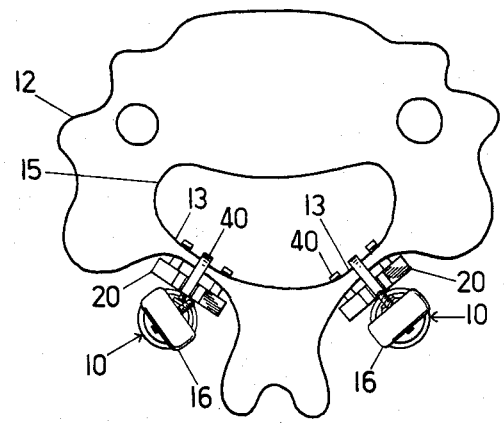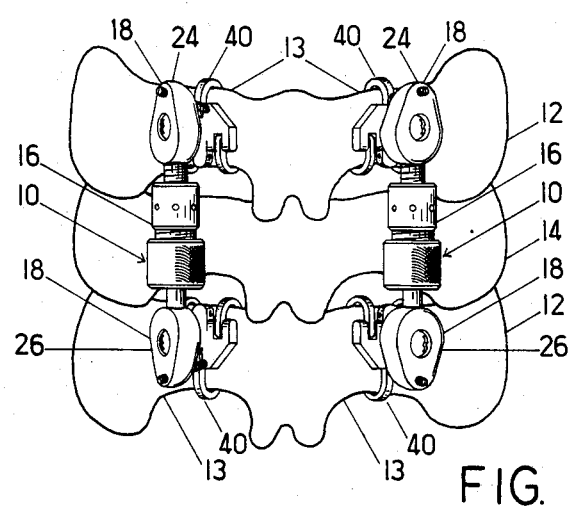
FIG. 1
FIG. 2
FIG. 4
FIG. 3

४,६११,५८२

VERTEBRAL CLAMP

TECHNICAL FIELD

The present invention relates to surgically implantable devices in general and, in particular to devices adapted to fix the spatial relationship between vertebrae.

BACKGROUND OF ART

Those skilled in the relevant art are cognizant of a variety of devices intended to be surgically implanted in a human patient to brace or otherwise affect the vertebral column. Many of these devices are adapted to fasten a series of vertebrae together by means of screws, clamps, and connective members. Examples include Lumb et al., U.S. Pat. No. 3,648,691; Crock et al., U.S. Pat. No. 3,997,138; McKay et al., U.S. Pat. No. 4,003,376; Hall, U.S. Pat. No. 4,041,939; Nissinen, U.S. Pat. No. 4,078,559; Miskew, U.S. Pat. No. 4,274,401; Dunn, U.S. Pat. No. 4,289,123; and Tanner, U.S. Pat. No. 4,361,141.

In all such devices, it is necessary to anchor the device to vertebrae in a way that is strong and secure and yet is not damaging to the vertebrae. Furthermore, it is desirable to minimize trauma generally and to guard against damage to the spinal cord running up through the vertebral column. These goals are accomplished in various ways in the devices referred to. In addition, in certain surgical procedures it is conventional to wire vertebrae, sometimes by threading wire beneath the vertebral lamina and carrying the wire back over the vertebral lamina before extending the wire to the next vertebra. It will be apparent that this process involves risk to the spinal cord located in the spinal foramen. Some devices are designed to engage individual vertebra with hooks that hook over the edge of the lamina without extending appreciably into the spinal foramen, thus minimizing risk to the spinal cord. Miskew discloses an example of such a device, as is the device shown in K. Roosen, A. Trauschel, and W. Grote, "Posterior Atlanto-Axial Fusion: A New Compression Clamp for Laminar Osteosynthesis," *Arch. Orthop. Traumat. Surg.* 100: 27–31 (1982).

In addition to providing for the secure clamping of such a device to the vertebrae, it is also desirable that the device be adjustable so that a single device may be adjusted to individual variations in the dimensions and relative locations of vertebrae in any given patient. In particular, when a device is being implanted to stabilize cervical vertebra injured traumatically or otherwise, adjustability of the device to meet the relative orientation and distance between the vertebrae is required.

With special reference to the surgical stabilization of fractures of cervical vertebrae, not only is it commonly necessary to stabilize adjacent vertebrae relative to each other, but it is also frequently necessary to bridge a damaged vertebra. For example, it might be found necessary to attach and stabilize the relationship between the third and fifth cervical vertebrae in such a way as to prevent the application of compressive pressures to the fourth cervical vertebra. Such stabilization is conventionally done with wire wrapped around various portions of the vertebrae and then tightened down. Additionally, bone grafts may be utilized to provide spacing and long-term support. Acrylic surgical cements mixed at the time of surgical intervention and hardened in place likewise may be used to provide support and set spacing and relative orientation. The wire that is used presents the dangers referred to above when it is passed underneath the laminae. In addition, several wires commonly are used to fasten the laminae together. Because the relative tension of each wire is only subjectively estimated, it is possible for such wires to break because of excess loading, requiring additional surgical intervention.

BRIEF SUMMARY OF THE INVENTION

The present invention is summarized in that a vertebral clamp adapted to control the spatial relationship between two vertebrae by attachment to the laminae thereof includes a longitudinally extended body having ends, the body being divided into a first half and a second half. The body has fastening means for adjusting the length of the body and fastening the first and second halves together. The vertebral clamp further includes two laminar clamps, one attached to each end of the body. Each laminar clamp is adapted to rigidly and securely clamp to a lamina of one of the vertebrae with the other laminar clamp similarly clamped to a lamina of the other vertebra.

A primary object of the invention is to provide an implantable vertebral clamp adapted to securely fasten to each of two vertebrae in order to aid in holding the vertebrae in a fixed, selected position relative to each other.

A second object of the invention is to provide such a clamp adapted to attach to the laminae of the vertebrae with a minimal danger to the spinal cord.

Another object of the invention is to provide such a clamp in which the part of the clamp that grasps the lamina of a vertebra is adjustable in orientation relative to the remainder of the clamp.

A further object of the invention is to provide such a clamp adjustable in overall length so that the distance between the clamped vertebrae may be adjusted and accommodated to.

Other objects, features, and advantages of the invention will be apparent from the following detailed description taken in conjunction with the accompanying drawings showing a preferred embodiment of a vertebral clamp exemplifying the principles of the invention.

BRIEF DESCRIPTION OF THE DRAWINGS

FIG. 1 is a side elevation view of a vertebral clamp made in accord with the present invention.

FIG. 2 is a perspective view of a portion of the vertebral clamp shown in FIG. 1.

FIG. 3 is a perspective view of three cervical vertebrae to the laminae of which have been applied two of the vertebral clamps shown in FIG. 1, the vertebrae being viewed generally from behind.

FIG. 4 is a perspective view of the vertebrae and vertebral clamps of FIG. 3 from above.

DETAILED DESCRIPTION OF THE PREFERRED EMBODIMENT

Figure 5:
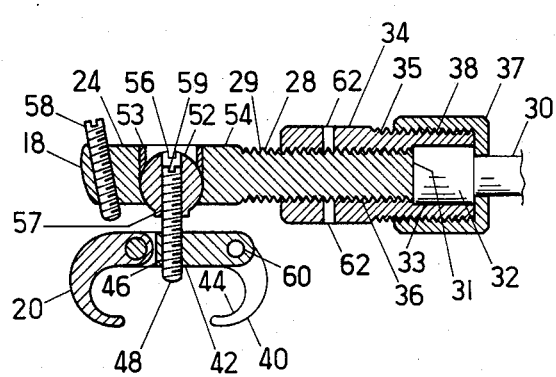
FIG. 5 is a cross sectional side view of the first end of the vertebral clamp of FIG. 1, taken along the longitudinal axis thereof.

Referring more particularly to the drawings, wherein like numbers refer to like parts, FIG. 1 shows a vertebral clamp, generally indicated at 10, made in accord with the present invention. The vertebral clamp 10 is adapted to attach to the laminae 13 of each of two clamped vertebrae 12 to hold them in a fixed spatial relation to each other. The clamped vertebrae 12 may be adjacent to each other or be separated by one or more unclamped vertebrae, such as that shown in FIG. 3 at 14. Each vertebra 12, 14 has laminae 13 and a spinal foramen 15.

The vertebral clamp 10 has a longitudinally extended body 16 with ends 18. The length of the body 16 is selected to be such that it spans the distance between the vertebrae 12 to be clamped, with one end 18 adjacent to each vertebra. A laminar clamp 20 is attached to each end 18 of the body 16. Each laminar clamp 20 is adapted to be rigidly and securely clamped to a lamina 13 of a vertebra 12, with the laminar clamp being further adapted to hold the lamina at a selected distance from the body 16. Preferably each laminar clamp 20 is so attached to the end 18 of the body 16 associated therewith that the laminar clamp may be tipped and rotated relative to the body with a selected degree of freedom.

The body 16 preferably includes and may be divided into a first half 24 and second half 26. The first half 24 includes a threaded shaft 28 that has male threads 29 and is oriented parallel to the longitudinal axis of the body 16. The second half 26 includes an unthreaded shaft 30 oriented parallel to the longitudinal axis of the body 16. At the end of the unthreaded shaft 30 remote from the laminar clamp 20 associated therewith is a retaining member 32, shown in FIG. 5. Preferably, the retaining member 32 is cylindrical and coaxial with the unthreaded shaft 30. The retaining member 32 has a diameter greater than those of the unthreaded shaft 30 and threaded shaft 28.

The body 16 further includes a tubular nut member 34. The nut member 34 has female threads 36 adapted to threadedly engage the threaded shaft 28. The nut member 34 also has a retention chamber 33 having an end 31 and opening towards the end of the nut member remote from the female threads 36. Preferably the end 31 is defined by the end of the threaded shaft 28 when it is engaged in the nut member, as is shown in FIG. 5. The retention chamber 33 is coaxial with the nut member 34 and is adapted to receive the retaining member 32 in freely turning relation. The nut member 34 also has male threads 35 on its external surface.

A cap 37 is mounted on the unthreaded shaft 30, turning freely thereon and retained thereon by the retaining member 32. The cap 37 has cap female threads 38 adapted to be engaged with the male threads 35 of the nut member 34. When so engaged, the cap 37 contains the retaining member 32 within the retention chamber 33 so that the nut member 34 and unthreaded shaft 30 are held together with their longitudinally axes substantially parallel. With the cap 37 partially turned down upon the male threads 35 of the nut member 34, the unthreaded shaft 30 and nut member may freely turn relative to each other, with their longitudinally axes held in alignment. If it is desired, the cap 37 may be sufficiently turned down upon the male threads 35 of the nut member 34, that the retaining member 32 may be held fast between the cap 37 and the end 31 of the retention chamber 33. When the cap 37 is engaged on the nut member 34 and so adjusted that the retaining member 32 and associated unthreaded shaft 30 can freely turn within the retention chamber 33, and with the threaded shaft 28 also threadedly engaged in the female threads 36 of the nut member, the first and second halves 24, 26 are effectively held together with the first and second halves free to rotate relative to each other about a common longitudinal axis.

Taken together, the threaded shaft 28, nut member 34, cap 37, and retaining member 32 constitute fastening means for adjusting the length of the body 16 and fastening the first and second halves 24, 26 together in such a fashion as to align their longitudinal axes and leave them free to turn relative to each other about their common longitudinal axis. The structure of the fastening means as disclosed is that preferred, although it will be apparent that other equivalent embodiments of such fastening means are possible. Thus, both the first and second halves 24, 26 could be equipped with male threads such as those shown at 29, one with left hand and other with right hand threads. The tubular nut member 34 could then be equipped with internal female threads, comparable to those shown at 36 but extending for the entire length of the tubular nut member, such threads being left handed for half the length of the nut member and right handed for the remaining half of the length and thus being adapted to threadedly engage the first and second halves 24, 26 simultaneously, one at each end of the nut member. That and all such alternative embodiments of the fastening means are within the scope and spirit of the invention.

The laminar clamps 20 each include at least two hooks 40 and a hook attachment member 42, the hooks being pivotably mounted on the hook attachment member. Each hook 40 extends away from the hook attachment member 42 for a selected distance and then curves toward the opposing hook or hooks to form a hook floor 44 presented toward the point of attachment. The curve of each hook 40 is such that a line drawn from a selected location on the hook floor 44 to the point of attachment is normal to the hook floor. Preferably each laminar clamp 20 includes three hooks 40, two mounted generally beside each other and separated by a selected distance with the third hook mounted in opposing relation at a point between them. This arrangement is best shown in FIG. 2. As a consequence of the shape and arrangement so disclosed, a vertebral lamina 13 may be held between the opposing hooks 40 in contact with the hook floors 44 thereof with a reduced tendency of the hooks to move away from each other with the effect of dislodging the lamina so held. The hooks 40 so shaped constitute retention means for retaining a vertebral lamina 13 within the hooks. Alternatively, such retention means could be provided by spring loading the hooks 40 or otherwise providing that they be urged toward each other to grip a lamina 13 between them. In addition the hooks 40 may be coated with a conventional, non-slip plastic such as polyurethane or be provided with an alternative non-slip surface, including ridges, serrations, and the like (not shown), to aid in securing a lamina 13 between opposing hooks. All such alternatives are within the scope and spirit of the invention.

The hook attachment member 42 is attached to an end 18 of the body 16 in such a way as to provide for ready adjustment of the angular orientation of the hook attachment member to the body. Preferably, the hook attachment member 42 has a threaded hole 46 extending therethrough. A clamping screw 48 is threadedly engaged in the hole 46. The clamping screw 48 is adapted to be turned down onto and press against a lamina 13 held between the hooks 40. The laminar end of the screw 48 is rounded so as to allow the entire hook attachment member 42 to tilt in the direction dictated by the forces imposed by the hooks 40. These hooks 40 grasp the lamina 12 as a result of the attachment member 42 moving away from the lamina 12 when the screw 48 is tightened upon the lamina 12. In addition, the parts of the clamping screw 48 adapted to contact a lamina 13 may be coated with a conventional, non-slip plastic such as polyurethane to aid in securing the lamina. By this means, the lamina 13 can be securely and rigidly held by the laminar clamp 20. The other end of the clamping screw 48 is attached to the body 16 by a ball and socket joint 50. The ball and socket joint 50 includes a ball 52 attached to the clamping screw 48 and a socket 54 adapted to receive and retain the ball in rotating relation. The ball 52 and socket 54 are best shown in phantom in FIG. 1 and in cross section in FIG. 5. The ball 52 is held within the socket 54 by a lock washer 53, shown in FIG. 5. Preferably the washer 53 is made of a high-friction plastic such as polyurethane to damp the movement of the ball.

Preferably the ball 52 has a slot 56 or comparable tool engaging means for engaging a turning tool in the ball, the slot being located in the ball at a point remote from its attachment to the clamping screw 48. When a lamina 13 is held between the hooks 40, the clamping screw 48 may be turned down upon the lamina by inserting an appropriate tool into the slot 56 and turning the ball 52. Preferably, the clamping screw 48 is threadedly engaged in a threaded hole running entirely through the ball 52. That end of the clamping screw 48 so engaged in the ball 52 is then provided with a second slot 59 or other tool engaging surface so that the clamping screw 48 may be turned down upon a lamina 13 held by the hooks 40, independent of movement of the ball 52. In addition, with the hook attachment member 42 and clamping screw 48 restrained from rotating (as would be the case when the laminar clamp 20 is applied to a lamina 13 with the clamping screw turned firmly down onto the lamina) the ball 52 may be independently turned, allowing the distance between the body 16 and hook attachment member to be adjusted.

Preferably at least one orientation fixating screw 58 is threadedly engaged in a hole extending through the body 16. The orientation fixating screw 58 is adapted to be turned until it makes contact with the hook attachment member 42, thereby restricting the movement of the ball 52, associated clamping screw 48, and hook attachment member. In addition, the hook attachment member 42 preferably has a aperture 60 extending therethrough at a selected point to provide a ready place to attach wires or sutures, as need might arise.

When used, the vertebral clamp 10 is adapted to fix the spatial relationship between two vertebrae 12 to be clamped, preferably when used in conjunction with a second vertebral clamp. After conventional surgical exposure of the necessary vertebral structures, the hooks 40 of one laminar clamp 20 are placed into position about one of the laminae 13 of a vertebra 12 to be clamped. The clamping screw 48 is turned down onto the lamina 13 with sufficient force to securely hold the lamina within the hooks 40. The hooks 40 are adapted to extend into the spinal foramen 15 to the minimum extent necessary to provide for a sufficiently secure grasp of the lamina 13.

With one laminar clamp 20 thus in place, the nut member 34 is turned to adjust the length of the body 16 until the remaining laminar clamp 20 of the vertebral clamp 10 is in position over the corresponding lamina 13 of the second vertebra 12 to be clamped. To facilitate adjustment of the nut member 34, it may be equipped with manipulating holes 62 generally spaced about its circumference. The manipulating holes 62 are adapted to receive and engage the end of conventional forceps or some other convenient surgical instrument, which then can be used to turn the nut member 34. The hooks 40 of the remaining laminar clamp 20 are put into place about that lamina 13 and the clamping screw 48 is turned down onto the lamina in the same manner that those steps were undertaken relative to the first vertebra 12 to be clamped.

The orientation fixating screws 58 associated with each laminar clamp 20 may be turned against the hook attachment member 42 thereof to stabilize the vertebral clamp 10 and fix the relative positions of the hook attachment members 42 to the body 16. If desired, wires or sutures can be passed through the apertures 60 and secured by attachment to selected tissues or parts of the vertebrae. A second vertebral clamp 10 may be put in place on the remaining laminae 13 of the vertebrae 12 to be clamped. The relative lengths of the two vertebral clamps 10 may then be set by adjustment of the nut members 34 thereof.

With the vertebral clamps 10 in place, it is preferred that a mold (not shown) be put in place about the vertebral clamps in the manner generally well known in the art. A selected surgical cement, such as an acrylic surgical cement, may then be mixed, put within the mold, and allowed to harden in place. Preferably such cement is allowed to intimately surround all of the moving parts of the vertebral clamps 10, locking them securely in place and protecting body tissues from contact with threads, corners, or other parts thereof that could prove irritating to such tissues. The manner of the use of such surgical cements is generally comparable to its use in procedures to wire vertebra, so that its mode of use is conventional and well known in the art. So applied, the vertebral clamps 10 of the invention provide secure bracing for the clamped vertebra 12 and may be permanently implanted in the patient's body.

All parts of the vertebral clamp 10 may be made of any rigid and strong material suitable for implantation in the body, including surgical steels and plastics. The vertebral clamp 10 may be made from such materials using conventional metal and plastic working techniques.

It is understood that the present invention is not imited to the particular construction and arrangement of parts illustrated and disclosed. Instead, it embraces all such modified forms thereof as come within the scope of the following claims.

What is claimed is:

1. A vertebral clamp adapted to control the spatial relationship between two vertebrae by attachment to the laminae thereof comprising:
  (a) a longitudinally extended body having ends, the body being divided into a first half and a second half and having fastening means for adjusting the length of the body and fastening the first and second halves together; and
  (b) two laminar clamps, one attached to each end of the body, each laminar clamp having means to rigidly and securely clamp to a lamina of one of the vertebrae with the other laminar clamp similarly clamped to a lamina of the other vertebra, each laminar clamp including
    (i) a hook attachment member adjustably attached to an end of the body and adapted to be adjusted in its angular orientation thereto, the hook attachment member having a threaded hole extending therethrough;

(ii) at least two hooks pivotably mounted on the hook attachment member at a point of attachment thereto, each hook curving generally toward an opposing hook to form a hook floor presented toward the point of attachment such that a line drawn from a selected location on the hook floor to the point of attachment is normal to the hook floor, whereupon a vertebral lamina may be held between the opposing hooks with a reduced tendency to be released by the hooks as a consequence of pressure exerted by the lamina in a direction away from the hook attachment member; and (iii) a clamping screw threadedly engaged in the threaded hole of the hook attachment member and adapted to be turned down onto and pressed against a vertebral lamina held between the hooks to securely and rigidly hold the lamina within the laminar clamp.

2. The vertebral clamp of claim 1 wherein the clamping screw is attached to a ball and the body includes a socket adapted to receive and retain the ball in rotating relation.

3. The vertebral clamp of claim 2 wherein the ball has a threaded hole extending therethrough and the clamping screw is threadedly engaged therein and adapted to be turned therein with relation to the ball, whereupon the distance from the hook attachment member to the body and the rotational relationship of the hook attachment member to the body both may be adjusted.

4. The vertebral clamp of claim 3 wherein the ball has a tool engaging means for engaging a selected tool in the ball, whereupon the ball and the laminar clamp attached thereto may be rotated relative to the body of the vertebral clamp independent of adjustment of the distance of the hook attachment member from the body and, when the clamping screw and hook attachment member are held in fixed relation to each other and are restrained from turning, the distance between the body and the hook attachment member may be adjusted independent of the rotational orientation of the hook attachment member relative to the body.

5. The vertebral clamp of claim 4 wherein the fastening means for adjusting the length of the body and fastening the first and second halves together includes a longitudinally extending threaded shaft forming a part of the first half of the body, a tubular nut member having female threads adapted to threadedly engage the threaded shaft, and means for attaching the nut member to the second half of the body coaxially therewith and in rotating relation thereto, whereby the female threads of the nut member may be threadedly engaged with the male threads of the threaded shaft to fasten the first and second halves together, aligning their longitudinal axes and leaving them free to turn relative to each other about their longitudinal axes, and the length of the body may be adjusted by turning the nut member on the threaded shaft.

6. The vertebral clamp of claim 4 wherein each end of the body has a threaded hole and an orientation fixating screw is threadedly engaged therein and adapted to be turned until it contacts the hook attachment member of a laminar clamp to restrict the movement of the laminar clamp relative to the body.

7. A vertebral clamp adapted to control the spatial relationship between two vertebrae by attachment to the laminae thereof comprising:

(a) a longitudinally extended body having ends, the body being divided into a first half and a second half and having fastening means for adjusting the length of the body and fastening the first and second halves together, the fastening means including means to align the longitudinal axes of the first and second halves of the body and leave them free to be turned relative to each other about their longitudinal axes to facilitate surgical attachment of the clamp to the vertebrae; and (b) two laminar clamps, one attached to each end of the body, each laminar clamp having means to rigidly and securely clamp to a lamina of one of the vertebrae with the other laminar clamp similarly clamped to a lamina of the other vertebra, each laminar clamp including (i) a hook attachment member adjustably attached to an end of the body and adapted to be adjusted in its angular orientation thereto, the hook attachment member having a threaded hole extending therethrough;

(ii) at least two hooks pivotably mounted on the hook attachment member at a point of attachment thereto, each hook curving generally toward an opposing hook to form a hook floor presented toward the point of attachment such that a line drawn from a selected location on the hook floor to the point of attachment is normal to the hook floor, whereupon a vertebral lamina may be held between the opposing hooks woth a reduced tendency to be released by the hooks as a consequence of pressure exerted by the lamina in a direction away from the hook attachment member; and (iii) a clamping screw threadedly engaged in the threaded hole of the hook attachment member and adapted to be turned down onto the pressed against a vertebral lamina held between the hooks to securely and rigidly hold the lamina within the laminar clamp.

8. The vertebral clamp of claim 7 wherein the clamping screw is attached to a ball and the body includes a socket adapted to receive and retain the ball in rotating relation.

9. The vertebral clamp of claim 8 wherein the ball has a threaded hole extending therethrough and the clamping screw is threadedly engaged therein and adapted to be turned therein with relation to the ball, whereupon the distance from the hook attachment member to the body and the rotational relationship of the hook attachment member to the body both may be adjusted.

10. The vertebral clamp of claim 9 wherein the ball has a tool engaging means for engaging a selected tool in the ball, whereupon the ball and the laminar clamp attached thereto may be rotated relative to the body of the vertebral clamp independent of adjustment of the distance of the hook attachment member from the body and, when the clamping screw and hook attachment member are held in fixed relation to each other and are restrained from turning, the distance between the body and the hook attachment member may be adjusted independent of the rotational orientation of the hook attachment member relative to the body.

11. The vertebral clamp of claim 10 wherein the fastening means for adjusting the length of the body and fastening the first and second halves together includes a longitudinally extending threaded shaft forming a part of the first half of the body, a tubular nut member having female threads adapted to threadedly engage the threaded shaft, and means for attaching the nut member to the second half of the body coaxially therewith and in rotating relation thereto, whereby the female threads of the nut member may be threadedly engaged with the male threads of the threaded shaft to fasten the first and second halves together, aligning their longitudinal axes and leaving them free to turn relative to rach other about their longitudinal axes, and the length of the body may be adjusted by turning the nut member on the threaded shaft.

12. The vertebral clamp of claim 10 wherein each end the body has a threaded hole and an orientation fixating screw is threadedly engaged therein and adapted to be turned until it contacts the hook attachment member of a laminar clamp to restrict the movement of the laminar clamp relative to the body.

* * * * *